United States Patent
Schmitt et al.

(10) Patent No.: US 7,449,584 B2
(45) Date of Patent: Nov. 11, 2008

(54) N-(2((4-HYDROXYPHENYL)AMINO) PYRIDIN-3-YL)-4-METHOXY BENZENESULFONAMIDE CRYSTALLINE FORM 1

(75) Inventors: Eric A. Schmitt, Libertyville, IL (US); Ira S. Buckner, Iowa City, IA (US); Geoff G. Z. Zhang, Libertyville, IL (US); Rodger F. Henry, Wildwood, IL (US)

(73) Assignee: Abbott Laboratories Inc., Abbott Park, IL (US)

( * ) Notice: Subject to any disclaimer, the term of this patent is extended or adjusted under 35 U.S.C. 154(b) by 0 days.

(21) Appl. No.: 11/331,865

(22) Filed: Jan. 13, 2006

(65) Prior Publication Data

US 2007/0099967 A1 May 3, 2007

Related U.S. Application Data

(60) Provisional application No. 60/643,553, filed on Jan. 13, 2005.

(51) Int. Cl.
C07D 213/76 (2006.01)
C07D 213/74 (2006.01)
(52) U.S. Cl. .................................... 546/307
(58) Field of Classification Search .................. 546/307
See application file for complete search history.

(56) References Cited

U.S. PATENT DOCUMENTS

| 5,250,549 A | 10/1993 | Yoshino et al. |
| 5,292,758 A | 3/1994 | Yoshino et al. |
| 2005/0075395 A1 | 4/2005 | Gordon et al. |
| 2006/0089391 A1 | 4/2006 | Gordon et al. |

OTHER PUBLICATIONS

Finazzi, Guido, et al, "Essential Thrombocythemia", *Seminars in Hematology*, 42(4): 230-238 (2005).
Lengfelder, Eva, et al., "Diagnosis and Therapy of Polycythemia Vera", *Seminars in Thrombosis and Hemostasis*, 32(3): 267-275 (2006).
Merrit, J.Christopher, et al., "The Efficacy and Safety of Perioperative Antiplatelet Therapy", *Journal of Thrombosis and Thrombolysis*, 17(1): 21-27 (2004).
Mitra, A.K., et al., "In Stent Restenosis: Bane of the Stent Era", *Journal of Clinical Pathology*, 59(3): 232-239 (2006).
Saw, Jacqueline, et al., "Antiplatelet Agents", *Platelet Function: Assessment, Diagnosis, and Treatment*, 335-367 (2005).
Weston, C., et al., "Antiplatelet Drugs in Cardiovascular Diseases", *International Journal of Clinical Practice*, 57(10): 898-905 (2006).

*Primary Examiner*—Patricia L Morris
(74) *Attorney, Agent, or Firm*—B. Gregory Donner

(57) ABSTRACT

N-(2-((4-Hydroxyphenyl)amino)pyridin-3-yl)-4-methoxybenzenesulfonamide Crystalline Form 1, ways to make it, compositions containing it and methods of treatment of diseases using it are disclosed.

1 Claim, No Drawings

US 7,449,584 B2

N-(2((4-HYDROXYPHENYL)AMINO) PYRIDIN-3-YL)-4-METHOXYBENZENE SULFONAMIDE CRYSTALLINE FORM 1

This application claims priority to co-pending U.S. Provisional Application Ser. No. 60/643,553, filed Jan. 13, 2005.

FIELD OF THE INVENTION

This invention pertains to N-(2-((4-Hydroxyphenyl) amino)pyridin-3-yl)-4-methoxybenzenesulfonamide Crystalline Form 1, ways to make it, compositions containing it and methods of treatment of diseases using it.

BACKGROUND OF THE INVENTION

Crystallinity of compounds may effect, among other physical and mechanical properties, their solubility, dissolution rate, hardness, compressibility and melting point. There is therefore an existing need in the chemical and therapeutic arts for identification of novel crystalline forms of salts of drugs and ways of reproducibly making them.

SUMMARY OF THE INVENTION

One embodiment of this invention pertains to N-(2-((4-Hydroxyphenyl)amino)pyridin-3-yl)-4-methoxybenzenesulfonamide Crystalline Form 1 characterized, when measured at about 25° C. with Cu—Kα radiation, by a powder diffraction pattern with at least three peaks having respective 2θ values of about 7.1°, 9.2°, 14.9°, 17.6°, 17.7°, 18.3°, 18.4°, 19.8°, 20.8°, 24.5°, 25.4°, or 28.2°.

Another embodiment pertains to N-(2-((4-Hydroxyphenyl)amino)pyridin-3-yl)-4-methoxybenzenesulfonamide Crystalline Form 1 characterized in the triclinic crystal system, when measured at about 25° C. with Mo—Kα radiation, by respective lattice parameters a, b and c and α, β and γ of 5.1731 Å±0.0001 Å, 12.7391 Å±0.0003 Å and 13.3853 Å±0.0001 Å and 95.412°, 99.114° and 98.176°.

Still another embodiment pertains to N-(2-((4-Hydroxyphenyl)amino)pyridin-3-yl)-4-methoxybenzenesulfonamide Crystalline Form 1 characterized in the triclinic crystal system, when measured at about 25° C. with Mo—Kα radiation, by respective lattice parameters a, b and c and α, β and γ of 5.1731 Å±0.0001 Å, 12.7391 Å±0.0003 Å and 13.3853 Å±0.0001 Å and 95.412°, 99.114° and 98.176°, respectively, and a powder diffraction pattern, when measured at about 25° C. with Cu—Kα radiation, with at least three peaks having respective 2θ values of about 7.1°, 9.2°, 14.9°, 17.6°, 17.7°, 18.3°, 18.4°, 19.8°, 20.8°, 24.5°, 25.4°, or 28.2°.

Still another embodiment pertains to N-(2-((4-Hydroxyphenyl)amino)pyridin-3-yl)-4-methoxybenzenesulfonamide Crystalline Form 1 having substantial crystalline purity and characterized, when measured at about 25° C. with Cu—Kα radiation, by a powder diffraction pattern with at least three peaks having respective 2θ values of about 7.1°, 9.2°, 14.9°, 17.6°, 17.7°, 18.3°, 18.4°, 19.8°, 20.8°, 24.5°, 25.4°, or 28.2°.

Still another embodiment pertains to N-(2-((4-Hydroxyphenyl)amino)pyridin-3-yl)-4-methoxybenzenesulfonamide Crystalline Form 1 having substantial crystalline purity and characterized in the triclinic crystal system, when measured at about 25° C. with Mo—Kα radiation, by respective lattice parameters a, b and c and α, β and γ of 5.1731 Å±0.0001 Å, 12.7391 Å±0.0003 Å and 13.3853 Å±0.0001 Å and 95.412°, 99.114° and 98.1760, respectively, and a powder diffraction pattern, when measured at about 25° C. with Cu—Kα radiation, with at least three peaks having respective 2θ values of about 7.1°, 9.2°, 14.9°, 17.6°, 17.7°, 18.3°, 18.4°, 19.8°, 20.8°, 24.5°, 25.4°, or 28.2°.

Still another embodiment pertains to N-(2-((4-Hydroxyphenyl)amino)pyridin-3-yl)-4-methoxybenzenesulfonamide Crystalline Form 1 having substantial crystalline purity and substantial chemical purity and characterized, when measured at about 25° C. with Cu—Kα radiation, by a powder diffraction pattern with at least three peaks having respective 2θ values of about 7.1°, 9.2°, 14.9°, 17.6°, 17.7°, 18.3°, 18.4°, 19.8°, 20.8°, 24.5°, 25.4°, or 28.2°.

Still another embodiment pertains to N-(2-((4-Hydroxyphenyl)amino)pyridin-3-yl)-4-methoxybenzenesulfonamide Crystalline Form 1 having substantial crystalline purity and substantial chemical purity and characterized in the triclinic crystal system, when measured at about 25° C. with Mo—Kα radiation, by respective lattice parameters a, b and c and α, β and γ of 5.1731 Å±0.0001 Å, 12.7391 Å±0.0003 Å and 13.3853 Å±0.0001 Å and 95.412°, 99.114° and 98.176°.

Still another embodiment pertains to N-(2-((4-Hydroxyphenyl)amino)pyridin-3-yl)-4-methoxybenzenesulfonamide Crystalline Form 1 having substantial crystalline purity and substantial chemical purity and characterized in the triclinic crystal system, when measured at about 25° C. with Mo—Kα radiation, by respective lattice parameters a, b and c and α, β and γ of 5.1731 Å±0.0001 Å, 12.7391 Å±0.0003 Å and 13.3853 Å±0.0001 Å and 95.412°, 99.114° and 98.176°, respectively, and a powder diffraction pattern, when measured at about 25° C. with Cu—Kα radiation, with at least three peaks having respective 2θ values of about 7.1°, 9.2°, 14.9°, 17.6°, 17.7°, 18.3°, 18.4°, 19.8°, 20.8°, 24.5°, 25.4°, or 28.2°.

Still another embodiment pertains to N-(2-((4-Hydroxyphenyl)amino)pyridin-3-yl)-4-methoxybenzenesulfonamide Crystalline Form 1 having substantial crystalline purity, substantial chemical purity and substantial geometric purity and characterized in the triclinic crystal system, when measured at about 25° C. with Mo—Kα radiation, by respective lattice parameters a, b and c and α, β and γ of 5.1731 Å±0.0001 Å, 12.7391 Å±0.0003 Å and 13.3853 Å±0.0001 Å and 95.412°, 99.114° and 98.176°.

Still another embodiment pertains to N-(2-((4-Hydroxyphenyl)amino)pyridin-3-yl)-4-methoxybenzenesulfonamide Crystalline Form 1 having substantial crystalline purity, substantial chemical purity and substantial geometric purity and characterized in the triclinic crystal system, when measured at about 25° C. with Mo—Kα radiation, by respective lattice parameters a, band c and α, β and γ of 5.1731 Å±0.0001 Å, 12.7391 Å±0.0003 Å and 13.3853 Å±0.0001 Å and 95.412°, 99.114° and 98.176°, respectively, and a powder diffraction pattern, when measured at about 25° C. with Cu—Kα radiation, with at least three peaks having respective 2θ values of about 7.1°, 9.2°, 14.9°, 17.6°, 17.7°, 18.3°, 18.4°, 19.8°, 20.8°, 24.5°, 25.4°, or 28.2°.

Still another embodiment pertains to compositions made with or comprising an excipient and a therapeutically acceptable amount of N-(2-((4-Hydroxyphenyl)amino)pyridin-3-yl)-4-methoxybenzenesulfonamide Crystalline Form 1 characterized, when measured at about 25° C. with Cu—Kα radiation, by a powder diffraction pattern with at least three peaks having respective 2θ values of about 7.1°, 9.2°, 14.9°, 17.6°, 17.7°, 18.3°, 18.4°, 19.8°, 20.8°, 24.5°, 25.4°, or 28.2°.

Still another embodiment pertains to compositions made with or comprising an excipient and therapeutically acceptable amount of N-(2-((4-Hydroxyphenyl)amino)pyridin-3-yl)-4-methoxybenzenesulfonamide Crystalline Form 1 characterized in the triclinic crystal system, when measured at about 25° C. with Mo—Kα radiation, by respective lattice parameters a, b and c and α, β and γ of 5.1731 Å±0.0001 Å, 12.7391 Å±0.0003 Å and 13.3853 Å±0.0001 Å and 95.412°, 99.114° and 98.176°.

Still another embodiment pertains to compositions made with or comprising an excipient and therapeutically accepted amount of N-(2-((4-Hydroxyphenyl)amino)pyridin-3-yl)-4-methoxybenzenesulfonamide Crystalline Form 1 characterized in the triclinic crystal system, when measured at about 25° C. with Mo—Kα radiation, by respective lattice parameters a, b and c and α, β and γ of 5.1731 Å±0.0001 Å, 12.7391 Å±0.0003 Å and 13.3853 Å±0.0001 Å and 95.412°, 99.114° and 98.176°, respectively, and a powder diffraction pattern, when measured at about 25° C. with Cu—Kα radiation, with at least three peaks having respective 2θ values of about 7.1°, 9.2°, 14.9°, 17.6°, 17.7°, 18.3°, 18.4°, 19.8°, 20.8°, 24.5°, 25.4°, or 28.2°.

Still another embodiment pertains to methods for treating cancer in a mammal comprising administering thereto a therapeutically effective amount of N-(2-((4-Hydroxyphenyl)amino)pyridin-3-yl)-4-methoxybenzenesulfonamide Crystalline Form 1 characterized, when measured at about 25° C. with Cu—Kα radiation, by a powder diffraction pattern with at least three peaks having respective 2θ values of about 7.1°, 9.2°, 14.9°, 17.6°, 17.7°, 18.3°, 18.4°, 19.8°, 20.8°, 24.5°, 25.4°, or 28.2°.

Still another embodiment pertains to methods for treating cancer in a mammal comprising administering thereto a therapeutically effective amount of N-(2-((4-Hydroxyphenyl)amino)pyridin-3-yl)-4-methoxybenzenesulfonamide Crystalline Form 1 characterized in the triclinic crystal system, when measured at about 25° C. with Mo—Kα radiation, by respective lattice parameters a, b and c and α, β and γ of 5.1731 Å±0.0001 Å, 12.7391 Å±0.0003 Å and 13.3853 Å±0.0001 Å and 95.412°, 99.114° and 98.176°.

Still another embodiment pertains to methods for treating cancer in a mammal comprising administering thereto a therapeutically effective amount of N-(2-((4-Hydroxyphenyl)amino)pyridin-3-yl)-4-methoxybenzenesulfonamide Crystalline Form 1 characterized in the triclinic crystal system, when measured at about 25° C. with Mo—Kα radiation, by respective lattice parameters a, b and c and α, β and γ of 5.1731 Å±0.0001 Å, 12.7391 Å±0.0003 Å and 13.3853 Å±0.0001 Å and 95.412°, 99.114° and 98.176°, respectively, and a powder diffraction pattern, when measured at about 25° C. with Cu—Kα radiation, with at least three peaks having respective 2θ values of about 7.1°, 9.2°, 14.9°, 17.6°, 17.7°, 18.3°, 18.4°, 19.8°, 20.8°, 24.5°, 25.4°, or 28.2°.

Still another embodiment pertains to processes for making N-(2-((4-Hydroxyphenyl)amino)pyridin-3-yl)-4-methoxybenzenesulfonamide Crystalline Form 1, said processes comprising:

providing a mixture comprising N-(2-((4-Hydroxyphenyl)amino)pyridin-3-yl)-4-methoxybenzenesulfonamide and solvent, wherein said N-(2-((4-Hydroxyphenyl)amino)pyridin-3-yl)-4-methoxybenzenesulfonamide is completely soluble in said solvent;

causing N-(2-((4-Hydroxyphenyl)amino)pyridin-3-yl)-4-methoxybenzenesulfonamide Crystalline Form 1 to exist in said mixture, said N-(2-((4-Hydroxyphenyl)amino)pyridin-3-yl)-4-methoxybenzenesulfonamide Crystalline Form 1 characterized, when isolated and measured at about 25° C. with Cu—Kα radiation, characterized by a powder diffraction pattern with at least three peaks having respective 2θ values of about 7.1°, 9.2°, 14.9°, 17.6°, 17.7°, 18.3°, 18.4°, 19.8°, 20.8°, 24.5°, 25.4°, or 28.2°; and isolating said N-(2-((4-Hydroxyphenyl)amino)pyridin-3-yl)-4-methoxybenzenesulfonamide Crystalline Form 1.

Still another embodiment pertains to N-(2-((4-Hydroxyphenyl)amino)pyridin-3-yl)-4-methoxybenzenesulfonamide Crystalline Form 1 prepared as described in the preceeding embodiment.

Still another embodiment pertains to processes for making N-(2-((4-Hydroxyphenyl)amino)pyridin-3-yl)-4-methoxybenzenesulfonamide Crystalline Form 1, said processes comprising:

providing a mixture comprising N-(2-((4-Hydroxyphenyl)amino)pyridin-3-yl)-4-methoxybenzenesulfonamide and solvent, wherein said N-(2-((4-Hydroxyphenyl)amino)pyridin-3-yl)-4-methoxybenzenesulfonamide is completely soluble in said solvent;

causing N-(2-((4-Hydroxyphenyl)amino)pyridin-3-yl)-4-methoxybenzenesulfonamide Crystalline Form 1 to exist in said mixture, said N-(2-((4-Hydroxyphenyl)amino)pyridin-3-yl)-4-methoxybenzenesulfonamide Crystalline Form 1 characterized, when isolated and measured at about 25° C. with Mo—Kα radiation, by respective lattice parameters a, b and c and α, β and γ of 5.1731 Å±0.0001 Å, 12.7391 Å±0.0003 Å and 13.3853 Å±0.0001 Å and 95.412°, 99.114° and 98.176°, respectively; and isolating said N-(2-((4-Hydroxyphenyl)amino)pyridin-3-yl)-4-methoxybenzenesulfonamide Crystalline Form 1.

Still another embodiment pertains to N-(2-((4-Hydroxyphenyl)amino)pyridin-3-yl)-4-methoxybenzenesulfonamide Crystalline Form 1 prepared as described in the preceeding embodiment.

Still another embodiment pertains to processes for making N-(2-((4-Hydroxyphenyl)amino)pyridin-3-yl)-4-methoxybenzenesulfonamide Crystalline Form 1, said processes comprising:

providing a mixture comprising N-(2-((4-Hydroxyphenyl)amino)pyridin-3-yl)-4-methoxybenzenesulfonamide and solvent, wherein said N-(2-((4-Hydroxyphenyl)amino)pyridin-3-yl)-4-methoxybenzenesulfonamide is completely soluble in said solvent;

causing N-(2-((4-Hydroxyphenyl)amino)pyridin-3-yl)-4-methoxybenzenesulfonamide Crystalline Form 1 to exist in said mixture, said crystalline N-(2-((4-Hydroxyphenyl)amino)pyridin-3-yl)-4-methoxybenzenesulfonamide Crystalline Form 1 characterized, when isolated and measured at about 25° C. with Mo—Kα radiation, by respective lattice parameters a, b and c and α, β and γ of 5.1731 Å±0.0001 Å, 12.7391 Å±0.0003 Å and 13.3853 Å±0.0001 Å and 95.412°, 99.114° and 98.176°, respectively; and a powder diffraction pattern, when measured at about 25°C. with Cu—Kα radiation, with at least three peaks having respective 2θ values of about 7.1°, 9.2°, 14.9°, 17.6°, 17.7°, 18.3°, 18.4°, 19.8°, 20.8°, 24.5°, 25.4°, or 28.2°; and isolating said N-(2-((4-Hydroxyphenyl)amino)pyridin-3-yl)-4-methoxybenzenesulfonamide Crystalline Form 1.

Still another embodiment pertains to N-(2-((4-Hydroxyphenyl)amino)pyridin-3-yl)-4-methoxybenzenesulfonamide Crystalline Form 1 prepared as described in the preceeding embodiment.

Still another embodiment pertains to processes for making N-(2-((4-Hydroxyphenyl)amino)pyridin-3-yl)-4-methoxybenzenesulfonamide Crystalline Form 1, said processes comprising:

providing a mixture comprising N-(2-((4-Hydroxyphenyl)amino)pyridin-3-yl)-4-methoxybenzenesulfonamide, n-propanol and water, wherein said N-(2-((4-Hydroxyphenyl)amino)pyridin-3-yl)-4-methoxybenzenesulfonamide is completely soluble in said n-propanol and water;

causing N-(2-((4-Hydroxyphenyl)amino)pyridin-3-yl)-4-methoxybenzenesulfonamide Crystalline Form 1 to exist in said mixture, said N-(2-((4-Hydroxyphenyl)amino)pyridin-3-yl)-4-methoxybenzenesulfonamide Crystalline Form 1 characterized, when isolated and measured at about 25° C. with Cu—Kα radiation, characterized by a powder diffraction pattern with at least three peaks having respective 2θ values of about 7.1°, 9.2°, 14.9°, 17.6°, 17.7°, 18.3°, 18.4°, 19.8°, 20.8°, 24.5°, 25.4°, or 28.2°; and isolating said N-(2-((4-Hydroxyphenyl)amino)pyridin-3-yl)-4-methoxybenzenesulfonamide Crystalline Form 1.

Still another embodiment pertains to N-(2-((4-Hydroxyphenyl)amino)pyridin-3-yl)-4-methoxybenzenesulfonamide Crystalline Form 1 prepared as described in the preceeding embodiment.

Still another embodiment pertains to processes for making N-(2-((4-Hydroxyphenyl)amino)pyridin-3-yl)-4-methoxybenzenesulfonamide Crystalline Form 1, said processes comprising:

providing a mixture comprising N-(2-((4-Hydroxyphenyl)amino)pyridin-3-yl)-4-methoxybenzenesulfonamide, n-propanol and water, wherein said N-(2-((4-Hydroxyphenyl)amino)pyridin-3-yl)-4-methoxybenzenesulfonamide is completely soluble in said n-propanol and water;

causing N-(2-((4-Hydroxyphenyl)amino)pyridin-3-yl)-4-methoxybenzenesulfonamide Crystalline Form 1 to exist in said mixture, said N-(2-((4-Hydroxyphenyl)amino)pyridin-3-yl)-4-methoxybenzenesulfonamide Crystalline Form 1 characterized, when isolated and measured at about 25° C. with Mo—Kα radiation, by respective lattice parameters a, b and c and α, β and γ of 5.1731 Å±0.0001 Å, 12.7391 Å±0.0003 Å and 13.3853 Å±0.0001 Å and 95.412°, 99.114° and 98.176°, respectively; and isolating said N-(2-((4-Hydroxyphenyl)amino)pyridin-3-yl)-4-methoxybenzenesulfonamide Crystalline Form 1.

Still another embodiment pertains to N-(2-((4-Hydroxyphenyl)amino)pyridin-3-yl)-4-methoxybenzenesulfonamide Crystalline Form 1 prepared as described in the preceeding embodiment.

Still another embodiment pertains to processes for making N-(2-((4-Hydroxyphenyl)amino)pyridin-3-yl)-4-methoxybenzenesulfonamide Crystalline Form 1, said processes comprising:

providing a mixture comprising N-(2-((4-Hydroxyphenyl)amino)pyridin-3-yl)-4-methoxybenzenesulfonamide, n-propanol and water, wherein said N-(2-((4-Hydroxyphenyl)amino)pyridin-3-yl)-4-methoxybenzenesulfonamide is completely soluble in said n-propanol and water;

causing N-(2-((4-Hydroxyphenyl)amino)pyridin-3-yl)-4-methoxybenzenesulfonamide Crystalline Form 1 to exist in said mixture, said crystalline N-(2-((4-Hydroxyphenyl)amino)pyridin-3-yl)-4-methoxybenzenesulfonamide Crystalline Form 1 characterized, when isolated and measured at about 25° C. with Mo—Kα radiation, by respective lattice parameters a, b and c and α, β and γ of 5.1731 Å±0.0001 Å, 12.7391 Å±0.0003 Å and 13.3853 Å±0.0001 Å and 95.412°, 99.114° and 98.176°, respectively; and a powder diffraction pattern, when measured at about 25° C. with Cu—Kα radiation, with at least three peaks having respective 2θ values of about 7.1°, 9.2°, 14.9°, 17.6°, 17.7°, 18.3°, 18.4°, 19.8°, 20.8°, 24.5°, 25.4°, or 28.2°; and isolating said N-(2-((4-Hydroxyphenyl)amino)pyridin-3-yl)-4-methoxybenzenesulfonamide Crystalline Form 1.

Still another embodiment pertains to N-(2-((4-Hydroxyphenyl)amino)pyridin-3-yl)-4-methoxybenzenesulfonamide Crystalline Form 1 prepared as described in the preceeding embodiment.

Still another embodiment pertains to processes for making N-(2-((4-Hydroxyphenyl)amino)pyridin-3-yl)-4-methoxybenzenesulfonamide Crystalline Form 1, said processes comprising:

providing a supersaturated mixture comprising N-(2-((4-Hydroxyphenyl)amino)pyridin-3-yl)-4-methoxybenzenesulfonamide, n-propanol and water at greater than about 60° C., wherein said N-(2-((4-Hydroxyphenyl)amino)pyridin-3-yl)-4-methoxybenzenesulfonamide is completely soluble in said n-propanol and water;

causing N-(2-((4-Hydroxyphenyl)amino)pyridin-3-yl)-4-methoxybenzenesulfonamide Crystalline Form 1 to exist in said mixture, said N-(2-((4-Hydroxyphenyl)amino)pyridin-3-yl)-4-methoxybenzenesulfonamide Crystalline Form 1 characterized, when isolated and measured at about 25° C. with Cu—Kα radiation, characterized by a powder diffraction pattern with at least three peaks having respective 2θ values of about 7.1°, 9.2°, 14.9°, 17.6°, 17.7°, 18.3°, 18.4°, 19.8°, 20.8°, 24.5°, 25.4°, or 28.2°; and isolating said N-(2-((4-Hydroxyphenyl)amino)pyridin-3-yl)-4-methoxybenzenesulfonamide Crystalline Form 1.

Still another embodiment pertains to N-(2-((4-Hydroxyphenyl)amino)pyridin-3-yl)-4-methoxybenzenesulfonamide Crystalline Form 1 prepared as described in the preceeding embodiment.

Still another embodiment pertains to processes for making N-(2-((4-Hydroxyphenyl)amino)pyridin-3-yl)-4-methoxybenzenesulfonamide Crystalline Form 1, said processes comprising:

providing a supersaturated mixture comprising N-(2-((4-Hydroxyphenyl)amino)pyridin-3-yl)-4-methoxybenzenesulfonamide, n-propanol and water at greater than about 60° C., wherein said N-(2-((4-Hydroxyphenyl)amino)pyridin-3-yl)-4-methoxybenzenesulfonamide is completely soluble in said n-propanol and water;

causing N-(2-((4-Hydroxyphenyl)amino)pyridin-3-yl)-4-methoxybenzenesulfonamide Crystalline Form 1 to exist in said mixture, said N-(2-((4-Hydroxyphenyl)amino)pyridin-3-yl)-4-methoxybenzenesulfonamide Crystalline Form 1 characterized, when isolated and measured at about 25° C. with Mo—Kα radiation, by respective lattice parameters a, b and c and α, β and γ of 5.1731 Å±0.0001 Å, 12.7391 Å±0.0003 Å and 13.3853 Å±0.0001 Å and 95.412°, 99.114° and 98.176°, respectively; and isolating said N-(2-((4-Hydroxyphenyl)amino)pyridin-3-yl)-4-methoxybenzenesulfonamide Crystalline Form 1.

Still another embodiment pertains to N-(2-((4-Hydroxyphenyl)amino)pyridin-3-yl)-4-methoxybenzenesulfonamide Crystalline Form 1 prepared as described in the preceding embodiment.

Still another embodiment pertains to processes for making N-(2-((4-Hydroxyphenyl)amino)pyridin-3-yl)-4-methoxybenzenesulfonamide Crystalline Form 1, said processes comprising:

providing a supersaturated mixture comprising N-(2-((4-Hydroxyphenyl)amino)pyridin-3-yl)-4-methoxybenzenesulfonamide, n-propanol and water at greater than about 60°

C., wherein said N-(2-((4-Hydroxyphenyl)amino)pyridin-3-yl)-4-methoxybenzenesulfonamide is completely soluble in said n-propanol and water;

causing N-(2-((4-Hydroxyphenyl)amino)pyridin-3-yl)-4-methoxybenzenesulfonamide Crystalline Form 1 to exist in said mixture, said crystalline N-(2-((4-Hydroxyphenyl)amino)pyridin-3-yl)-4-methoxybenzenesulfonamide Crystalline Form 1 characterized, when isolated and measured at about 25° C. with Mo—Kα radiation, by respective lattice parameters a, b and c and α, β and γ of 5.1731 Å±0.0001Å, 12.7391 Å±0.0003 Å and 13.3853 Å±0.0001 Å and 95.412°, 99.114° and 98.176°, respectively, and a powder diffraction pattern, when measured at about 25° C. with Cu—Kα radiation, with at least three peaks having respective 2θ values of about 7.1°, 9.2°, 14.9°, 17.6°, 17.7°, 18.3°, 18.4°, 19.8°, 20.8°, 24.5°, 25.4°, or 28.2°; and isolating said N-(2-((4-Hydroxyphenyl)amino)pyridin-3-yl)-4-methoxybenzenesulfonamide Crystalline Form 1.

Still another embodiment pertains to N-(2-((4-Hydroxyphenyl)amino)pyridin-3-yl)-4-methoxybenzenesulfonamide Crystalline Form 1 prepared as described in the preceeding embodiment.

Still another embodiment pertains to processes for making N-(2-((4-Hydroxyphenyl)amino)pyridin-3-yl)-4-methoxybenzenesulfonamide Crystalline Form 1, said processes comprising:

causing nucleation in mixture of N-(2-((4-hydroxyphenyl)amino)pyridin-3-yl)-4-methoxybenzenesulfonamide and solvent between about 60° C. and 100° C., wherein the N-(2-((4-hydroxyphenyl)amino)pyridin-3-yl)-4-methoxybenzenesulfonamide is completely dissolved in the solvent and the solvent is supersaturated with the N-(2-((4-hydroxyphenyl)amino)pyridin-3-yl)-4-methoxybenzenesulfonamide and isolating said N-(2-((4-Hydroxyphenyl)amino)pyridin-3-yl)-4-methoxybenzenesulfonamide Crystalline Form 1.

Still another embodiment pertains to N-(2-((4-Hydroxyphenyl)amino)pyridin-3-yl)-4-methoxybenzenesulfonamide Crystalline Form 1 prepared as described in the preceeding embodiment.

Still another embodiment pertains to N-(2-((4-Hydroxyphenyl)amino)pyridin-3-yl)-4-methoxybenzenesulfonamide Crystalline Form 2 for use in preparing N-(2-((4-Hydroxyphenyl)amino)pyridin-3-yl)-4-methoxybenzenesulfonamide Crystalline Form 1.

Still another embodiment pertains to amorphous N-(2-((4-hydroxyphenyl)amino)pyridin-3-yl)-4-methoxybenzenesulfonamide for use in preparing N-(2-((4-Hydroxyphenyl)amino)pyridin-3-yl)-4-methoxybenzenesulfonamide Crystalline Form 1.

Still another embodiment pertains to amorphous or crystalline N-(2-((4-hydroxyphenyl)amino)pyridin-3-yl)-4-methoxybenzenesulfonamide hydrochloride for use in preparing N-(2-((4-Hydroxyphenyl)amino)pyridin-3-yl)-4-methoxybenzenesulfonamide Crystalline Form 1.

Still another embodiment pertains to crystalline or non crystalline N-(2-((4-hydroxyphenyl)amino)pyridin-3-yl)-4-methoxybenzenesulfonamide methanolate for use in preparing N-(2-((4-Hydroxyphenyl)amino)pyridin3-yl)-4-methoxybenzenesulfonamide Crystalline Form 1.

Still another embodiment pertains to crystalline or non crystalline N-(2-((4-hydroxyphenyl)amino)pyridin-3-yl)-4-methoxybenzenesulfonamide ethanolate for use in preparing N-(2-((4-Hydroxyphenyl)amino)pyridin-3-yl)-4-methoxybenzenesulfonamide Crystalline Form 1.

DETAILED DESCRIPTION OF THE INVENTION

This invention pertains to discovery of a crystalline form of N-(2-((4-hydroxyphenyl)amino)pyridin-3-yl)-4-methoxybenzenesulfonamide, ways to make it having substantial crystalline and chemical purity, ways to characterize it, compositions containing it, and methods of treating diseases using it.

The term "crystalline," as used herein, means having a regularly repeating arrangement of molecules or external face planes.

The term "N-(2-((4-Hydroxyphenyl)amino)pyridin-3-yl)-4-methoxybenzenesulfonamide Crystalline Form 1, " as used herein, means a crystalline form of N-(2-((4-hydroxyphenyl)amino)pyridin-3-yl)-4-methoxybenzenesulfonamide that is metastable at 25° C. and characterized in the triclinic crystal system, when measured at about 25° C. with Mo—Kα radiation, by respective lattice parameters a, b and c and α, β and γ of 5.1731 Å±0.0001 Å, 12.7391 Å±0.0003 Å and 13.3853 Å±0.0001 Å and 95.412°, 99.114° and 98.176°, respectively, by a powder diffraction pattern, when measured at about 25° C. with Cu—Kα radiation, with at least three peaks having respective 2θ values of about 7.1°, 9.2°, 14.9°, 17.6°, 17.7°, 18.3°, 18.4°, 19.8°, 20.8°, 24.5°, 25.4°, or 28.2°, or by a combination thereof.

N-(2-((4-hydroxyphenyl)amino)pyridin-3-yl)-4-methoxybenzenesulfonamide may also be written as $R^1SO_2NHR^2$, wherein $R^1$ is 4-methoxyphenyl and $R^2$ is 2-((4-hydroxyphenyl)aminopyridin-3-yl.

The term "metastable," as used herein, means other than the most thermodynamically stable crystalline form at a particular temperature.

The term "substantial crystalline purity," as used herein, means at least about 95% crystalline purity, preferably about 97% crystalline purity, more preferably about 99% crystalline purity, and most preferably about 100% crystalline purity.

The term "crystalline purity," as used herein, means percentage of N-(2-((4-Hydroxyphenyl)amino)pyridin-3-yl)-4-methoxybenzenesulfonamide Crystalline Form 1 in a sample that may contain amorphous N-(2-((4-Hydroxyphenyl)amino)pyridin-3-yl)-4-methoxybenzenesulfonamide, one or more than one of a crystalline form of N-(2-((4-Hydroxyphenyl)amino)pyridin-3-yl)-4-methoxybenzenesulfonamide other than N-(2-((4-Hydroxyphenyl)amino)pyridin-3-yl)-4-methoxybenzenesulfonamide Crystalline Form 1 or a mixture thereof.

The term "supersaturated," as used herein, means having a compound in a solvent in which it is completely dissolved at a certain temperature but at which the solubility of the compound in the solvent at that certain temperature is exceeded.

The term "substantial chemical purity," as used herein, means about 95% chemical purity, preferably about 97% chemical purity, more preferably about 98% chemical purity, and most preferably about 100% chemical purity.

The term "chemical purity," as used herein, means percentage of N-(2-((4-hydroxyphenyl)amino)pyridin-3-yl)-4-methoxybenzenesulfonamide in a sample that may also contain, for example, acetic acid, ethanol, ethyl acetate, isopropyl acetate, isopropyl ether, methanol, n-propanol, pyridine, pyridine hydrochloride, water, 4-aminophenol, 3,4-bis(4-hydroxyanilino)-6 -((4-hydroxyphenyl)imino)-2,4-cyclohexadien-1-one of varying geometric purity, 2-chloro-3-nitropyridine or a regioisomer thereof, 2,6-di-tert-butylphenol, 4-((3-nitro-2-pyridinyl)oxy)aniline, para-methoxybenzenesulfonyl chloride, 4-((3-(((4-methoxyphenyl)sulfonyl)amino)pyridin-2-yl)amino)phenyl 4-methoxybenzenesulfonate or a mixture thereof.

The term "substantial geometric purity," as used herein, means geometric isomeric excess greater than about 95%, preferably greater than about 97%, more preferably greater than about 99%, and most preferably about 100%.

The term "geometric isomeric excess," as used herein, means amount of one geometric isomer of a compound in a mixture which may have another geometric isomer of the same compound in the mixture.

The term "amorphous," as used herein, means a supercooled liquid or a viscous liquid wthat looks like a solid but does not have a regularly repeating arrangement of molecules that is maintained over a long range and does not have a melting point but rather softens or flows above its glass transition temperature.

The term "mixture," as used herein, means a combination of two or more than two substances. For mixtures comprising N-(2-((4-hydroxyphenyl)amino)pyridin-3-yl)-4-methoxybenzenesulfonamide and solvent, the N-(2-((4-hydroxyphenyl)amino)pyridin-3-yl)-4-methoxybenzenesulfonamide may be completely soluble, partially soluble, or essentially insoluble in the solvent.

It is meant to be understood that solvent molecules of solvated N-(2-((4-hydroxyphenyl)amino)pyridin-3-yl)-4-methoxybenzenesulfonamide may be used as solvent for preparation of N-(2-((4-Hydroxyphenyl)amino)pyridin-3-yl)-4-methoxybenzenesulfonamide Crystalline Form 1.

The term "solvate," as used herein, means including a solvent therewith such as acetic acid, acetone, acetonitrile, benzene, chloroform, carbon tetrachloride, dichloromethane, dimethylsulfoxide, 1,4-dioxane, ethanol, ethyl acetate, butanol, tert-butanol, N,N-dimethyl-acetamide, N,N-dimethylformamide, formamide, formic acid, heptane, hexane, isopropanol, methanol, 1-methyl-2-pyrrolidinone, mesitylene, nitromethane, polyethylene glycol, propanol, 2-propanone, pyridine, tetrahydrofuran, toluene, water, xylene, or a mixture thereof.

Causing crystalline N-(2-((4-Hydroxyphenyl)amino)pyridin-3-yl)-4-methoxybenzenesulfonamide Crystalline Form 1 to exist in a mixture comprising N-(2-((4-hydroxyphenyl)amino)pyridin-3-yl)-4-methoxybenzenesulfonamide and solvent, wherein the N-(2-((4-hydroxyphenyl)amino)pyridin-3-yl)-4-methoxybenzenesulfonamide is completely soluble in the solvent, is known as nucleation.

Nucleation may be made to occur by means such as solvent removal, temperature change, solvent-miscible anti-solvent addition, solvent-immiscible anti-solvent addition, seed crystal addition of N-(2-((4-Hydroxyphenyl)amino)pyridin-3-yl)-4-methoxybenzenesulfonamide Crystalline Form 1, chafing or scratching the interior of the container, preferably a glass container, in which nucleation is meant to occur with an implement such as a glass rod or a glass bead or beads, or a combination of the foregoing.

For the practice of this invention, nucleation may be followed by crystal growth, accompanied by crystal growth, or followed and accompanied by crystal growth during which N-(2-((4-Hydroxyphenyl)amino)pyridin-3-yl)-4-methoxybenzenesulfonamide Crystalline Form 1 having substantial crystalline purity develops.

In a preferred embodiment for the practice of this invention, N-(2-((4-Hydroxyphenyl)amino)pyridin-3-yl)-4-methoxybenzenesulfonamide Crystalline Form 1 is prepared by causing nucleation in mixture of N-(2-((4-hydroxyphenyl)amino)pyridin-3-yl)-4-methoxybenzenesulfonamide and solvent between about 60° C. and 100° C., wherein the N-(2-((4-hydroxyphenyl)amino)pyridin-3-yl)-4-methoxybenzenesulfonamide is completely dissolved in the solvent and the solvent is supersaturated with the N-(2-((4-hydroxyphenyl)amino)pyridin-3-yl)-4-methoxybenzenesulfonamide.

It is meant to be understood that N-(2-((4-Hydroxyphenyl)amino)pyridin-3-yl)-4-methoxybenzenesulfonamide Crystalline Form 2, amorphous N-(2-((4-hydroxyphenyl)amino)pyridin-3-yl)-4-methoxybenzenesulfonamide amorphous or crystalline N-(2-((4-hydroxyphenyl)amino)pyridin-3-yl)-4-methoxybenzenesulfonamide hydrochloride, crystalline or non crystalline N-(2-((4-hydroxyphenyl)amino)pyridin-3-yl)-4-methoxybenzenesulfonamide methanolate, crystalline or non crystalline N-(2-((4-hydroxyphenyl)amino)pyridin-3-yl)-4-methoxybenzenesulfonamide ethanolate or mixtures thereof may be used to prepare mixtures of N-(2-((4-hydroxyphenyl)amino)pyridin-3-yl)-4-methoxybenzenesulfonamide and solvent, wherein the N-(2-((4-hydroxyphenyl)amino)pyridin-3-yl)-4-methoxybenzenesulfonamide is completely soluble in the solvent.

N-(2-((4-Hydroxyphenyl)amino)pyridin-3-yl)-4-methoxybenzenesulfonamide Crystalline Form 2 is described in commonly-owned U.S. patent application Ser. No. 11/332,020

Amorphous N-(2-((4-hydroxyphenyl)amino)pyridin-3-yl)-4-methoxybenzenesulfonamide N-(2-((4-Hydroxyphenyl)amino)pyridin-3-yl)-4-methoxybenzenesulfonamide is described in commonly-owned U.S. patent application Ser. No. 11/332,275

Amorphous N-(2-((4-Hydroxyphenyl)amino)pyridin-3-yl)-4-methoxybenzenesulfonamide hydrochloride is described in commonly-owned U.S. patent application Ser. No. 11/332,408

Crystalline N-(2-((4-Hydroxyphenyl)amino)pyridin-3-yl)-4-methoxybenzenesulfonamide hydrochloride is described in commonly-owned U.S. patent application Ser. No. 11/332,015

N-(2-((4-Hydroxyphenyl)amino)pyridin-3-yl)-4-methoxybenzenesulfonamide ethanolate is described in commonly-owned U.S. patent application Ser. No. 11/332,274

N-(2-((4-Hydroxyphenyl)amino)pyridin-3-yl)-4-methoxybenzenesulfonamide methanolate is described in commonly-owned U.S. patent application Ser. No. 11/331,535

The term "solvent," as used herein, means a substance, preferably a liquid or a miscible, partially miscible or essentially immiscible mixture of two or more than two liquids, which is capable of completely dissolving, partially dissolving, dispersing or partially dispersing another substance, preferably a solid or a mixture of solids.

The term "miscible," as used herein, means capable of combining without separation of phases.

The term "anti-solvent," as used herein, means a solvent in which N-(2-((4-hydroxyphenyl)amino)pyridin-3-yl)-4-methoxybenzenesulfonamide is essentially insoluble.

It is meant to be understood that, because many solvents and anti-solvents contain impurities, the level of impurities in solvents and anti-solvents for the practice of this invention, if present, are at a low enough percentage that they do not interfere with the intended use of the solvent in which they are present.

It is also meant to be understood that airborne seed crystals of crystalline N-(2-((4-Hydroxyphenyl)amino)pyridin-3-yl)-4-methoxybenzenesulfonamide Crystalline Form 1 may also cause nucleation in a mixture of N-(2-((4-hydroxyphenyl)amino)pyridin-3-yl)-4-methoxybenzenesulfonamide Crystalline Form 1 and solvent.

The term "seed crystal," as used herein, means N-(2-((4-Hydroxyphenyl)amino)pyridin-3-yl)-4-methoxybenzenesulfonamide Crystalline Form 1 having mass. It is meant to be understood that such a crystal may be small enough to be airborne or invisible to the eye.

The term "isolating" or "isolation," as used herein, means separating N-(2-((4-Hydroxyphenyl)amino)pyridin-3-yl)-4-methoxybenzenesulfonamide Crystalline Form 1 and impurity, wherein the impurity may be solvent, anti-solvent, a solid or a mixture thereof. Isolation of N-(2-((4-Hydroxyphenyl)amino)pyridin-3-yl)-4-methoxybenzenesulfonamide Crystalline Form 1 is typically accomplished by means such as centrifugation, filtration with or without vacuum, filtration under positive pressure, distillation, evaporation or a combination thereof.

EXAMPLE 1

4-((3-nitropyridin-2-yl)amino)phenol

A mixture of 2-chloro-3-nitropyridine (2C3NP, 138.1 Kg), 4-aminophenol (2.5-3 equivalents) and N,N-dimethylformamide (DMF, 4.8 mL/g 2C3NP) was stirred until homogeneous, heated at 50° C. during which an exotherm raised the solution temperature to 70° C., warmed to 80-85° C., stirred until no 2-chloro-3-nitropyridine remained, cooled to 30° C., treated with water (10.6 mL/g 2C3NP) to precipitate product, then with acetic acid (1.2 mL/g 2C3NP), then with ethyl acetate (0.5 mL/g 2C3NP), cooled to 5° C., stirred for 2 hours and filtered. The filtrant was washed sequentially with distilled water (1.6 mL/g 2C3NP), cold ethanol (1.2 mL/g 2C3NP) and cold isopropyl ether (1.2 mL/g 2C3NP), and dried under vacuum.

In a preferred embodiment of this process, 4-aminophenol (1 equivalent) was used with 4-methylmorpholine (1.5 equivalents) in either methanol or DMF, and precipitation was accomplished with 10% aqueous acetic acid.

EXAMPLE 2

4-((3-aminopyridin-2-yl)amino)phenol

A mixture of EXAMPLE 1 (41.05 Kg) and ammonium formate (5 equivalents), with or without 2,6-di-tert-butylphenol antioxidant, was treated with a mixture of 50% wet 5% palladium hydroxide on carbon (7% by weight per weight of EXAMPLE 1), in DMF (6 mL/g catalyst) then DMF (total DMF volume: 5 mL/g EXAMPLE 1) first with moderate agitation to control an exotherm (typically peaking at 85° C.) then with increased agitation for 1 hour (incomplete reactions were treated with additional catalyst/DMF mixture), cooled to 10° C., and filtered. The filtrant was washed with DMF (0.4 mL/g EXAMPLE 1), and the filtrate was added to water (29.4 mL/g EXAMPLE 1) at 10° C. to precipitate a solid which was filtered, washed with water (7.5 mL/g EXAMPLE 1), partially dried under a nitrogen stream, and further dried under vacuum at 50° C. to about 0.5% moisture.

EXAMPLE 3

N-(2-((4-hydroxyphenyl)amino)pyridin-3-yl)-4-methoxybenzenesulfonamide

A mixture of EXAMPLE 2 in pyridine (9 mL/g) at 0° C. was treated with a mixture of para-methoxybenzenesulfonyl chloride (1.05 equivalents) in THF (1.4 mL/g) at 0° C. at a rate which kept the reaction temperature below 5° C., warmed to 25° C., stirred for 15 minutes, and concentrated. The concentrate was treated with n-propanol to provide a composition having 9% pyridine in the solvent mixture and to precipitate a solid. The mixture was cooled to 0° C. and filtered. The filtrant and washed with ethyl acetate (5-7 mL/g starting material) and dried at 45° C.

EXAMPLE 4A

N-(2-((4-Hydroxyphenyl)amino)pyridin-3-yl)-4-methoxybenzenesulfonamide

Crystalline Form 1

Crystallization of EXAMPLE 3 was preformed by cooling a mixture of N-(2-((4-hydroxyphenyl)amino)pyridin-3-yl)-4-methoxybenzenesulfonamide (180 mg/g solvent) and 69:31 n-propanol/water at 78° C., wherein the N-(2-((4-hydroxyphenyl)amino)pyridin-3-yl)-4-methoxybenzenesulfonamide was completely soluble in the solvent, to 30° C. over 2 hours, filtering immediately and drying the filtrant.

EXAMPLE 4B

N-(2-((4-Hydroxyphenyl)amino)pyridin-3-yl)-4-methoxybenzenesulfonamide Crystalline Form 1 was also made by providing a mixture of N-(2-((4-hydroxyphenyl)amino)pyridin-3-yl)-4-methoxybenzenesulfonamide and 1:1 acetone/water at about 25° C., wherein the N-(2-((4-hydroxyphenyl)amino)pyridin-3-yl)-4-methoxybenzenesulfonamide was completely soluble in the solvent, causing N-(2-((4-Hydroxyphenyl)amino)pyridin-3-yl)-4-methoxybenzenesulfonamide Crystalline Form 1 to exist in the mixture by treating the mixture with water anti-solvent over 1.5 hours with a syringe pump so that the solvent part of the mixture changed from 50% acetone to 10% acetone, seeding the mixture with N-(2-((4-Hydroxyphenyl)amino)pyridin-3-yl)-4-methoxybenzenesulfonamide Crystalline Form 1 and filtering the mixture and immediately drying the filtrant.

A sample of N-(2-((4-Hydroxyphenyl)amino)pyridin-3-yl)-4-methoxybenzenesulfonamide Crystalline Form 1 for powder diffraction analysis was applied as a thin layer, with no prior grinding, to the analysis well of a Scintag XDS 2000 Diffractometer having the following parameters: x-ray source: Cu—K$\alpha$ ; range: 2.00°-40.00° 2$\theta$; scan rate: 1.00 degree per minute; step size: 0.02°; temperature: about 25° C.; wavelength: 1.54178 Å.

Representative characteristic peak positions in the powder diffraction pattern of N-(2-((4-Hydroxyphenyl)amino)pyridin-3-yl)-4-methoxybenzenesulfonamide Crystalline Form 1, expressed as degrees relative to 2$\theta$, are, when measured at about 25° C. with Cu—K$\alpha$ radiation, about 7.1°(0,1,0), 9.2° (1,1,-1), 14.1° (0,2,0), 14.9° (0,2,-1), 17.6° (1,0,0), 17.7° (1,0,-1), 18.3° (-1,-1,-1), 18.4° (0,2,-2), 19.8° (1,1,-1), 20.8° (0,2,2), 24.5° (1,0,-3), 25.4° (1,-1,3), or 28.2° (1,-2,-3). Each peak position is shown with its accompanying Miller index (hkl) values.

The term "about" preceeding a series of peak positions is meant to include all of the peak positions of the group which the term precedes.

It is meant to be understood that peak heights may vary and will be dependent on variables such as the temperature, size of crystal size or morphology, sample preparation, or sample height in the analysis well of the diffractometer.

It is also meant to be understood that peak positions may vary when measured with different radiation sources. For example, Cu—K$\alpha_1$, Mo—K$\alpha$, Co—K$\alpha$ and Fe—K$\alpha$ radiation, having wavelengths of 1.54060 Å, 0.7107 Å, 1.7902 Å and 1.9373 Å, respectively, may provide peak positions which differ from those measured with Cu—Kα radiation.

While digital outputs from powder x-ray diffractometers may be set to express peak positions to the one-hundredth and one-thousandth of a degree past the decimal, diffractometers are incapable of accurate experimental determination beyond one-tenth of a degree. Accordingly, peak positions reported herein are rounded to one-tenth of a degree past the decimal.

Peak positions may also be expressed with a variability which accounts for differences between powder x-ray diffractometers, and variability between Cu—Kα radiation sources, variability from sample to sample on the same diffractometer, and differences in sample heights in the analysis well. This variability is preferably expressed as about ±0.2°, about ±0.1°, or a combination thereof.

Therapeutic utility of N-(2-((4-hydroxyphenyl)amino)pyridin-3-yl)-4-methoxybenzenesulfonamide is demonstrated in commonly-owned U.S. application Ser. No. 10/857,235, May 28, 2004 and U.S. Application Ser. No. 60/575,577, May 28, 2004, the specifications of which are hereby incorporated by reference into this application.

N-(2-((4-Hydroxyphenyl)amino)pyridin-3-yl)-4-methoxybenzenesulfonamide binds to the colchicine site of tubulin β-subunits and inhibits the polymerization of tubulin. Accordingly, the compound is useful as a drug for treating diseases in a mammal which are caused or exacerbated by polymerization of tubulin. Such diseases include, but are not limited to, cancer and gouty arthritis, wherein cancer includes, but is not limited to, bone marrow dyscrasias, breast (ductal and lobular) cancer, cervical cancer, colon cancer, gastric cancer, leukemia, lung (small cell and non-small cell) cancer, lymphoma, melonoma, mouth and tongue cancer, neuroblastoma (including pediatric neuroblastoma), oral cancerpancreatic cancer, prostate cancer, rectal cancer, renal cancer, sarcoma, stomach cancer, uterine cancer, and cancers resulting from the metastasis of disease from these areas.

The term "mammal," as used herein, means a particular class of vertebrate, preferably a human.

Compositions made with or comprising N-(2-((4-Hydroxyphenyl)amino)pyridin-3-yl)-4-methoxybenzenesulfonamide Crystalline Form 1 may be administered, for example, bucally, ophthalmically, orally, osmotically, parenterally (intramuscularly, intraperintoneally, intrasternally, intravenously, subcutaneously), rectally, topically, transdermally, or vaginally. Ophthalmically administered dosage forms may be administered as, for example, elixirs, emulsions, microemulsions, oinments, solutions, suspensions, or syrups. Orally administered solid dosage forms may be administered as, for example, capsules, dragees, emulsions, granules, pills, powders, solutions, suspensions, tablets, microemulsions, elixirs, syrups, or powders for reconstitution. Osmotically and topically administered dosage forms may be administered as, for example, creams, gels, inhalants, lotions, ointments, pastes, or powders. Parenterally administered dosage forms may be administered, as, for example, aqueous or oleaginous solutions or suspensions. Rectally and vaginally dosage forms may be administered as, for example, creams, gels, lotions, ointments or pastes.

A preferred formulation for the practice of this invention is shown in TABLE 1.

TABLE 1

| Ingredient | % (w/w) |
| --- | --- |
| N-(2-((4-Hydroxyphenyl)-amino)pyridin-3-yl)-4-methoxybenzenesulfonamide | 30.0 |

TABLE 1-continued

| Ingredient | % (w/w) |
| --- | --- |
| Crystalline Form 1 | |
| microcrystalline cellulose NF (Avicel ® PH101) | 15.8 |
| lactose monohydrate | 28.0 |
| povidone (USP, K29-32) | 8.0 |
| croscarmellose Na | 18.0 |
| water | sufficient quantity |
| magnesium stearate | 0.2 |

The therapeutically acceptable amount of crystalline N-(2-((4-Hydroxyphenyl)amino)pyridin-3-yl)-4-methoxybenzenesulfonamide Crystalline Form 1 depends on recipient of treatment, the disease and severity thereof, the composition containing it, time of administration, route of administration, duration of treatment, its potency, its rate of clearance and whether or not another drug is co-administered. The amount of N-(2-((4-Hydroxyphenyl)amino)pyridin-3-yl)-4-methoxybenzenesulfonamide Crystalline Form 1 used to make a composition to be administered daily to a patient in a single dose or in divided doses is from about 0.03 to about 200 mg/kg body weight. Single dose compositions contain these amounts or a combination of submultiples thereof.

N-(2-((4-Hydroxyphenyl)amino)pyridin-3-yl)-4-methoxybenzenesulfonamide Crystalline Form 1 may be administered with or without an excipient. Excipients include, but are not limited to, encapsulating materials and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, and mixtures thereof.

Excipients for preparation of compositions comprising N-(2-((4-Hydroxyphenyl)amino)pyridin-3-yl)-4-methoxybenzenesulfonamide Crystalline Form 1 to be administered orally in solid dosage Form 1 include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions made with N-(2-((4-Hydroxyphenyl)amino)pyridiri3-yl)-4-methoxybenzenesulfonamide Crystalline Form 1 to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, and mixtures thereof. Excipients for preparation of compositions made with N-(2-((4-Hydroxyphenyl)amino)pyridin-3-yl)-4-methoxybenzenesulfonamide Crystalline Form 1 to be administered osmotically include, for example, chlorofluorohydrocarbons, ethanol, water, and mixtures thereof. Excipients for preparation of compositions made with N-(2-((4-Hydroxyphenyl)amino)pyridin-3-yl)-4-methoxybenzenesulfonamide Crystalline Form 1 to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, and mixtures thereof. Excipients for preparation of compositions made with or comprising N-(2-((4-Hydroxyphenyl)amino)pyridin-3-yl)-4-methoxybenzenesulfonamide Crystalline Form 1 to be administered rectally or vaginally include, for example, cocoa butter, polyethylene glycol, wax, and mixtures thereof.

The foregoing is meant to be illustrative of the invention and not intended to limit it to the disclosed embodiments. Variations and changes obvious to one skilled in the art are intended to be within the scope and nature of the invention as defined in the claims.

The invention claimed is:

1. A process for making N-(2-((4-Hydroxyphenyl)amino)pyridin-3-yl)-4-methoxybenzenesulfonamide Crystalline Form 1, said processes comprising:

causing nucleation in mixture of N-(2-((4-hydroxyphenyl)amino)pyridin-3-yl)-4-methoxybenzenesulfonamide and solvent between about 60° C. and 100° C., wherein the N-(2-((4-hydroxyphenyl)amino)pyridin-3-yl)-4-methoxybenzenesulfonamide is completely dissolved in the solvent and the solvent is supersaturated with the N-(2-((4-hydroxyphenyl)amino)pyridin-3-yl)-4-methoxybenzenesulfonamide and isolating said N-(2-((4-Hydroxyphenyl)amino)pyridin-3-yl)-4-methoxybenzenesulfonamide Crystalline Form 1.

* * * * *

UNITED STATES PATENT AND TRADEMARK OFFICE
CERTIFICATE OF CORRECTION

PATENT NO. : 7,449,584 B2  Page 1 of 1
APPLICATION NO. : 11/331865
DATED : November 11, 2008
INVENTOR(S) : Schmitt et al.

It is certified that error appears in the above-identified patent and that said Letters Patent is hereby corrected as shown below:

Title Page, item (54), under "Title", in Column 1, Line 1, delete "(2((4" and insert -- (2-((4 --.

Column 1, Line 1, delete "(2((4" and insert -- (2-((4 --.

Column 16, Line 7, in claim 1, delete "3 -yl)" and insert -- 3-yl) --.

Column 16, Line 9, in claim 1, delete "3 -yl)" and insert -- 3-yl) --.

Column 16, Line 13, in claim 1, delete "3 -yl)" and insert -- 3-yl) --.

Column 16, Line 15, in claim 1, delete "3 -yl)" and insert -- 3-yl) --.

Signed and Sealed this

Twenty-ninth Day of June, 2010

David J. Kappos
*Director of the United States Patent and Trademark Office*